(12) United States Patent
Chowhan et al.

(10) Patent No.: US 8,388,941 B2
(45) Date of Patent: *Mar. 5, 2013

(54) SELF PRESERVED AQUEOUS PHARMACEUTICAL COMPOSITIONS

(75) Inventors: Masood A. Chowhan, Arlington, TX (US); David J. Keith, Washington, MO (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/441,995

(22) PCT Filed: Sep. 20, 2007

(86) PCT No.: PCT/US2007/079094
§ 371 (c)(1),
(2), (4) Date: Mar. 19, 2009

(87) PCT Pub. No.: WO2008/042619
PCT Pub. Date: Apr. 10, 2008

(65) Prior Publication Data
US 2010/0021562 A1     Jan. 28, 2010

Related U.S. Application Data

(60) Provisional application No. 60/827,417, filed on Sep. 28, 2006.

(51) Int. Cl.
*A61K 9/00* (2006.01)
(52) U.S. Cl. .................. 424/78.04; 514/738; 514/912
(58) Field of Classification Search ............... 424/78.04; 514/738, 912
See application file for complete search history.

(56) References Cited

U.S. PATENT DOCUMENTS

| | | | |
|---|---|---|---|
| 4,522,806 A | 6/1985 | Muhlemann et al. |
| 5,130,298 A | 7/1992 | Cini et al. |
| 5,221,664 A | 6/1993 | Berkowitz et al. |
| 5,320,843 A | 6/1994 | Raheja et al. |
| 5,352,708 A | 10/1994 | Woodward et al. |
| 5,424,078 A | 6/1995 | Dziabo et al. |
| 5,460,834 A | 10/1995 | Bhagat |
| 5,597,559 A | 1/1997 | Olejnik et al. |
| 5,607,698 A | 3/1997 | Martin et al. |
| 5,683,993 A | 11/1997 | Tsao |
| 5,725,887 A | 3/1998 | Martin et al. |
| 5,736,165 A | 4/1998 | Ripley et al. |
| 5,741,817 A | 4/1998 | Chowhan et al. |
| 5,817,277 A | 10/1998 | Mowrey-McKee et al. |
| 5,820,822 A | 10/1998 | Kross |
| 5,858,346 A | 1/1999 | Vehige et al. |
| 5,858,996 A | 1/1999 | Tsao |
| 6,017,861 A | 1/2000 | Fujiwara et al. |
| 6,024,954 A | 2/2000 | Park et al. |
| 6,034,043 A | 3/2000 | Fujiwara et al. |
| 6,121,315 A | 9/2000 | Nair et al. |
| 6,143,799 A | 11/2000 | Chowhan et al. |
| 6,319,464 B1 | 11/2001 | Asgharian |
| 6,348,190 B1 | 2/2002 | Illes et al. |
| 6,482,799 B1 | 11/2002 | Tuse et al. |
| 6,492,361 B1 | 12/2002 | Muller et al. |
| 6,503,497 B2 | 1/2003 | Chowhan et al. |
| 6,583,124 B2 | 6/2003 | Asgharian |
| 7,074,827 B2 | 7/2006 | Ueno |
| 7,445,771 B2 | 11/2008 | Dassanayake et al. |
| 2002/0122831 A1 | 9/2002 | Mowrey-McKee et al. |
| 2002/0123482 A1 | 9/2002 | Chowhan et al. |
| 2005/0129771 A1 | 6/2005 | Asgharian |
| 2005/0214382 A1 | 9/2005 | Xia et al. |
| 2006/0205725 A1 | 9/2006 | Ueno |
| 2007/0212420 A1 | 9/2007 | Xia et al. |
| 2007/0297990 A1 | 12/2007 | Shah et al. |
| 2008/0075790 A1 | 3/2008 | Kabra et al. |
| 2010/0227003 A1 | 9/2010 | Shah et al. |
| 2011/0195132 A1 | 8/2011 | Kabra et al. |

FOREIGN PATENT DOCUMENTS

| | | |
|---|---|---|
| JP | 2003-104870 | 4/2003 |
| WO | 95/13050 | 5/1995 |
| WO | 98/10773 | 3/1998 |
| WO | 2005/097067 | 10/2005 |
| WO | 2007/106723 | 9/2007 |
| WO | 2008/036847 | 3/2008 |
| WO | 2008/042619 | 4/2008 |

OTHER PUBLICATIONS

Guttman, "Liquid gel therapy broadens role of dry eye product line", Ophthalmologytimes.com, 2006, pp. 33-34 and copyright notice.
Illustration of packaging for Systane® free.
Hoffman H.M. et al., "Pre-clinical in vitro Testing of an Artificial Tear Formulation with a Novel Preservation System", poster presentation at the annual meeting of the Association for Research in Vision and Ophthalmology (ARVO), Ft. Lauderdale, FL., Apr. 30, 2006.
Illustration of packaging for Systane® Free, Mar. 7, 2006.
Systane® Free promotional document (minimal-blur) published on or about Jan. 1, 2006.
Kabara, et al., Preservative-Free and Self-Preserving Cosmetics and Drugs—Principles and Practice, Chapter 1, pp. 1-14, Marcel Dekker, Inc., 1997.
McCarthy, "Metal Ions and Microbial Inhibitors", Cosmetic & Toiletries, 100:69-72, 1985.
McCarthy, et al., "The Effect of Zinc Ions on the Antimicrobial Activity of Selected Preservatives", Journal of Pharmacy and Pharmacology, vol. 41 (1989).
PCT International Preliminary Report on Patentability for corresponding application PCT/US2007/079094 with mailing date Dec. 11, 2008.
PCT International Search Report for corresponding application PCT/US2007/079094 with mailing date Apr. 2, 2008.

(Continued)

Primary Examiner — Zohreh Fay
(74) Attorney, Agent, or Firm — Scott A. Chapple

(57) ABSTRACT

The use of a borate/polyol and zinc system to enhance the antimicrobial activity of multi-dose pharmaceutical compositions is described. The compositions do not require a conventional anti-microbial preservative and therefore are referred to as being 'self-preserved'. The compositions possess sufficient antimicrobial activity to satisfy the preservative efficacy requirements of the USP for aqueous ophthalmic compositions.

10 Claims, No Drawings

OTHER PUBLICATIONS

PCT Written Opinion for corresponding application PCT/US2007/079094 with mailing date Apr. 2, 2008.

Zeelie, et al., "Effects of Copper and Zinc Ions on the Germicidal Properties of Two Popular Pharmaceutical Antiseptic Agents, Cetylpyridinium Chloride and Povidone-iodine", Analyst, 123:503-507 (Mar. 1998).

Zeelie, et al., "The Effects of Selected Metal Salts on the Microbial Activities of Agents used in the Pharmaceutical and Related Industries", Metal Compounds in Environment and Life, 4:193-200 (1992).

Bruce Grahn et al., "Zinc and the Eye", Journal of the American College of Nutrition, 106-118, Apr. 2001.

SELF PRESERVED AQUEOUS PHARMACEUTICAL COMPOSITIONS

This application claims priority as a 371 application from PCT/US2007/079094 filed on Sep. 20, 2007, and claims priority from U.S. Ser. No. 60/827,417, filed on Sep. 28, 2006.

BACKGROUND OF THE INVENTION

The present invention is directed to self-preserved pharmaceutical compositions. More specifically, the invention is directed to the provision of aqueous, multi-dose pharmaceutical compositions that have been formulated so as to have sufficient antimicrobial activity to satisfy the preservation efficacy requirements of the United States Pharmacopeia ("USP") and analogous guidelines in other countries, without requiring a conventional antimicrobial preservative, such as benzalkonium chloride, polyquaternium-1, hydrogen peroxide (e.g., sodium perborate), or chorine-containing agents. The ability to achieve self-preservation is based on a unique combination of formulation components and criteria.

Many pharmaceutical compositions are required to be sterile (i.e., free of bacteria, fungi and other pathogenic microorganisms). Examples of such compositions include: solutions and suspensions that are injected into the bodies of humans or other mammals; creams, lotions, solutions or other preparations that are topically applied to wounds, abrasions, burns, rashes, surgical incisions, or other conditions where the skin is not intact; and various types of compositions that are applied either directly to the eye (e.g., artificial tears, irrigating solutions, and drug products), or are applied to devices that will come into contact with the eye (e.g., contact lenses).

The foregoing types of compositions can be manufactured under sterile conditions via procedures that are well known to those skilled in the art. However, once the packaging for a product is opened, such that the composition contained therein is exposed to the atmosphere and other sources of potential microbial contamination (e.g., the hands of a human patient), the sterility of the product may be compromised. Such products are typically utilized multiple times by the patient, and are therefore frequently referred to as being of a "multi-dose" nature.

Due to the frequent, repeated exposure of multi-dose products to the risk of microbial contamination, it is necessary to employ a means for preventing such contamination from occurring. The means employed may be: (i) a chemical agent that prevents the proliferation of microbes in a composition, which is referred to herein as an "antimicrobial preservative"; or (ii) a packaging system that prevents or reduces the risk of microbes reaching a pharmaceutical composition within a container.

Prior multi-dose ophthalmic compositions have generally contained one or more antimicrobial preservations in order to prevent the proliferation of bacteria, fungi and other microbes. Such compositions may come into contact with the cornea either directly or indirectly. The cornea is particularly sensitive to exogenous chemical agents. Consequently, in order to minimize the potential for harmful effects on the cornea, it is preferable to use anti-microbial preservatives that are relatively non-toxic to the cornea, and to use such preservatives at the lowest possible concentrations (i.e., the minimum amounts required in order to perform their anti-microbial functions).

Balancing the anti-microbial efficacy and potential toxicological effects of anti-microbial preservatives is sometimes difficult to achieve. More specifically, the concentration of an antimicrobial agent necessary for the preservation of ophthalmic formulations from microbial contamination may create the potential for toxicological effects on the cornea and/or other ophthalmic tissues. Using lower concentrations of the anti-microbial agents generally helps to reduce the potential for such toxicological effects, but the lower concentrations may be insufficient to achieve the required level of biocidal efficacy (i.e., antimicrobial preservation).

The use of an inadequate level of antimicrobial preservation may create the potential for microbial contamination of the compositions and ophthalmic infections resulting from such contaminations. This is also a serious problem, since ophthalmic infections involving *Pseudomonas aeruginosa* or other virulent microorganisms can lead to loss of visual function or even loss of the eye.

Thus, there is a need for a means of enhancing the activity of anti-microbial agents so that very low concentrations of the agents can be utilized without increasing the potential for toxicological effects or subjecting patients to unacceptable risks of microbial contamination and resulting ophthalmic infections.

Ophthalmic compositions are generally formulated as isotonic, buffered solutions. One approach to enhancing the anti-microbial activity of such compositions is to include multi-functional components in the compositions. In addition to performing their primary functions, these multi-functional components also serve to enhance the overall anti-microbial activity of the compositions.

The following publications may be referred to for further background regarding the use of multi-functional components to enhance the antimicrobial activity of ophthalmic compositions:

1. U.S. Pat. No. 5,817,277 (Mowrey-McKee, et al; tromethamine);
2. U.S. Pat. No. 6,503,497 (Chowhan, et al.; borate/polyol complexes);
3. U.S. Pat. No. 5,741,817 (Chowhan, et al.; low molecular weight amino acids such as glycine);
4. U.S. Pat. No. 6,319,464 (Asgharian; low molecular weight amino alcohols); and
5. U.S. Patent Application Publication No. US 2002/0122831 A1 (Mowrey-McKee, et al.; bis-aminopolyols).

The present invention is also based in-part on a finding that zinc further enhances the antimicrobial activity of ophthalmic compositions containing borate/polyol complexes of the type described herein. The use of zinc to enhance the antimicrobial activity of pharmaceutical compositions, including ophthalmic solutions, is well known. See, for example, the following articles and patent publications, as well as U.S. Pat. No. 6,348,190 and JP 2003-104870, cited above:

McCarthy, "Metal Ions and Microbial Inhibitors", *Cosmetic & Toiletries,* 100:69-72 (February 1985);
Zeelie, et al., "The Effects of Selected Metal Salts on the Microbial Activities of Agents used in the Pharmaceutical and Related Industries", *Metal Compounds in Environment and Life,* 4:193-200 (1992);
Zeelie, et al., "Effects of Copper and Zinc Ions on the Germicidal Properties of Two Popular Pharmaceutical Antiseptic Agents, Cetylpyridinium Chloride and Povidone-iodine", *Analyst,* 123:503-507 (March 1998);
McCarthy, et al., "The Effect of Zinc Ions on the Antimicrobial Activity of Selected Preservatives", *Journal of Pharmacy and Pharmacology,* Vol. 41 (1989);
U.S. Pat. No. 6,482,799 (Tuśe, et al.);
U.S. Pat. No. 5,320,843 (Raheja, et al.);
U.S. Pat. No. 5,221,664 (Berkowitz, et al.);
U.S. Pat. No. 6,034,043 (Fujiwara, et al.);
U.S. Pat. No. 4,522,806 (Muhlemann, et al.);

U.S. Pat. No. 6,017,861 (Fujiwara, et al.); and
U.S. Pat. No. 6,121,315 (Nair, et al.).
However, the use of zinc ions in combination with borate/polyol complexes, as described herein is not disclosed or suggested by the prior art.

The compositions of the present invention are multi-dose products that do not contain a conventional antimicrobial preservative (e.g., benzalkonium chloride), but yet are preserved from microbial contamination. Such compositions have been referred to in the art as being "preservative free" (see, e.g., U.S. Pat. No. 5,597,559 issued to Olejnik, et al.). Compositions that are preserved from microbial contamination as a result of the inherent antimicrobial activity of one or more components of the compositions are also referred to in the art as being "self-preserved" (see, e.g., U.S. Pat. No. 6,492,361 issued to Muller, et al.).

The following publication may be referred to for further background regarding pharmaceutical compositions that are "preservative-free" or "self-preserving": Kabara, et al., *Preservative-Free and Self-Preserving Cosmetics and Drugs—Principles and Practice*, Chapter 1, pages 1-14, Marcel Dekker, Inc. (1997).

The multi-dose compositions of the present invention, which do not contain a conventional antimicrobial preservative are referred to herein as being "self-preserved".

SUMMARY OF THE INVENTION

The present invention is based on a finding that zinc is capable of enhancing the antimicrobial activity of aqueous pharmaceutical compositions containing borate/polyol complexes, when utilized as described herein, so as to create aqueous, multi-dose compositions that satisfy the preservative efficacy requirements of the USP without a conventional antimicrobial preservative.

The self-preserved, multi-dose compositions of the present invention have several advantages over existing ophthalmic formulations that are either: (i) packaged as a "single dose" or "unit of use" product, so as to avoid the inclusion of any antimicrobial preservative (e.g., BION®TEARS Lubricant Eye Drops, which is marketed by Alcon Laboratories, Inc.), or (ii) preserved by means of a so-called "disappearing" preservatives, such as the chlorite-based system described in U.S. Pat. Nos. 5,424,078; 5,736,165; 6,024,954; and 5,858,346 (e.g., the artificial tears product "REFRESH™ Tears", which is marketed by Allergan), or the peroxide-containing system described in U.S. Pat. Nos. 5,607,698; 5,683,993; 5,725,887; and 5,858,996 (e.g., the artificial tear product "GenTeal™ Tears", which is marketed by CIBA Vision).

Unlike these existing products, the multi-dose ophthalmic compositions of the present invention are able to satisfy the USP preservative efficacy requirements without employing any conventional antimicrobial preservatives, such as chlorite or hydrogen peroxide.

The above-discussed findings regarding the zinc may be applied to enhance the antimicrobial activity of various types of pharmaceutical compositions. However, the present invention is particularly directed to the provision of aqueous ophthalmic solutions that are effective in preventing microbial contamination in the absence of conventional antimicrobial preservatives, such as benzalkonium chloride ("BAC"), polyquaternium-1, chlorite or hydrogen peroxide.

DETAILED DESCRIPTION OF THE INVENTION

The pharmaceutical compositions of the present invention contain a borate/polyol complex and zinc ions in amounts sufficient to enhance the antimicrobial activity of the compositions, such that a conventional antimicrobial preservative is not required.

As used herein, the term "borate" includes boric acid, salts of boric acid, other pharmaceutically acceptable borates, and combinations thereof. The following borates are particularly preferred: boric acid, sodium borate, potassium borate and combinations thereof. The use of borates containing divalent cations (e.g., calcium borate) may adversely affect the antimicrobial action of zinc ions, by competing with zinc for binding sites on the cell walls of bacterial and other microbes, and is therefore not preferred. For the same reason, the self-preserved compositions of the present invention are preferably free of or substantially free of other sources of divalent cations, such as calcium chloride.

As used herein, the term "polyol" includes any compound having at least one hydroxyl group on each of two adjacent carbon atoms that are not in trans configuration relative to each other. The polyols can be linear or cyclic, substituted or unsubstituted, or mixtures thereof, so long as the resultant complex is water soluble and pharmaceutically acceptable. Examples of such compounds include: sugars, sugar alcohols, sugar acids and uronic acids. Preferred polyols are sugars, sugar alcohols and sugar acids, including, but not limited to: mannitol, glycerin, xylitol, sorbitol and propylene glycol. The use of sorbitol, propylene glycol, or a combination thereof is particularly preferred.

The self-preserved compositions of the present invention preferably contain one or more borates in an amount of from about 0.1 to about 2.0% w/v, more preferably 0.3 to 1.5% w/v, and most preferably 0.5 to 1.2% w/v. The compositions of the present invention preferably contain one or more polyols in an amount of from about 0.01 to about 5.0% w/v, more preferably 0.6 to 2.0% w/v.

The use of borate-polyol complexes to enhance antimicrobial activity is described in U.S. Pat. No. 6,503,497 (Chowhan, et al.), the entire contents of which are hereby incorporated in the present specification by reference. The above-described borate/polyol complexes are utilized in the compositions of the present invention in an amount effective to enhance the antimicrobial activity of the composition. The total concentration of the borate/polyol complex will typically be in the range of 0.5 to 6.0 percent by weight ("wt. %").

The zinc may be provided in various forms, such as zinc chloride, zinc sulfate, zinc acetate or zinc carbonate. The use of zinc chloride is preferred. The amount of zinc chloride required to achieve this effect may vary somewhat from formulation to formulation, depending on the particular borate/polyol complex selected, but will generally be from about 0.0005% to about 0.005% w/v, preferably 0.00075 to 0.0025% w/v.

In general, the self-preserved compositions of the present invention will preferably contain zinc, either in the form of zinc chloride or other zinc salts, at a molar concentration of 0.000017 moles/liter to 0.00017 moles/liter, preferably 0.000026 moles/liter to 0.00009 moles/liter. However, the concentration of zinc may be as high as 0.0035 moles/liter.

The manner in which zinc enhances antimicrobial activity in the compositions of the present invention is not completely understood. However, it is believed that zinc atoms enhance the antimicrobial activity of borates by forming bridges between the borate groups The present invention is particularly directed to the provision of multi-dose, self-preserved ophthalmic compositions that contain zinc and borate in amounts sufficient to allow the compositions to satisfy the USP preservative efficacy requirements, as well as other preservative efficacy standards for aqueous pharmaceutical compositions, without a conventional antimicrobial preservative.

Relative to bacteria, the USP 27 Antimicrobial Effectiveness Test requires that multi-dose ophthalmic compositions have sufficient antimicrobial activity to reduce an initial inoculum of approximately $10^5$ to $10^6$ bacteria by one log (i.e., a 90% reduction in the microorganism population) over a period of seven (7) days and by three logs (i.e., a 99.9% reduction in the microorganism population) over a period of fourteen (14) days, and requires that there cannot be any increase in the microorganism population following the conclusion of the fourteen day period. Relative to fungi, the USP standards require that the compositions maintain stasis (i.e., no growth) relative to the population of the initial inoculum over the entire 28 day test period. The margin of error in calculating microorganism populations is generally accepted to be 0.5 logs. Accordingly, the term "stasis" as utilized relative to the above-discussed USP standards means that the initial fungi population cannot increase by more than 0.5 log orders, relative to the initial population.

The preservative efficacy standards for multi-dose ophthalmic solutions in the U.S. and other countries/regions are set forth in the following table:

ence (or absence) of other ingredients in the composition (e.g., chelating agents, buffering agents and/or tonicity agents). The amino alcohol will generally be present in an amount necessary to enhance the antimicrobial activity of an aqueous self-preserved pharmaceutical composition of the type described herein. The amount of amino alcohol required for a particular composition can be determined through comparative testing, such as the tests described in Example 6 hereof. The above-described amino alcohols are also utilized in the compositions of the present invention to neutralize the pH of the borate or borate/polyol complex, or bring the composition to the desired pH level. The amount of amino alcohol required for this purpose is a function of the particular borate or borate/polyol mixture selected and the concentration thereof. In general, the self-preserved compositions of the present invention will contain one or more amino alcohols at a total concentration of from about 0.01 to about 2.0 percent by weight/volume ("% w/v"), and preferably from 0.1 to 1.0% w/v.

The zinc and borate/polyol preservative systems described herein may be included in various types of pharmaceutical compositions to enhance anti-microbial activity and self-preserve the compositions, such as ophthalmic, otic, nasal and

| | Preservative Efficacy Test ("PET") Criteria (Log Order Reduction of Microbial Inoculum Over Time | |
|---|---|---|
| | Bacteria | Fungi |
| USP 27 | A reduction of 1 log (90%), by day 7; 3 logs (99.9%) by day 14; and no increase after day 14 | The compositions must demonstrate over the entire test period, which means no increases of 0.5 logs or greater, relative to the initial inoculum. |
| Japan | 3 logs by 14 days; and no increase from day 14 through day 28. | No increase from initial count at 14 and 28 days |
| Ph. Eur. A[1] | A reduction of 2 logs (99%) by 6 hours; 3 logs by 24 hours; and no recovery after 28 days | A reduction of 2 logs (99%) by 7 days, and no increase thereafter |
| Ph. Eur. B | A reduction of 1 log at 24 hours; 3 logs by day 7; and no increase thereafter | A reduction of 1 log (90%) by day 14, and no increase thereafter |
| FDA/ISO 14730 | A reduction of 3 logs from initial challenge at day 14; and a reduction of 3 logs from rechallenge | No increase higher than the initial value at day 14, and no increase higher than the day 14 rechallenge count through day 28. |

[1]There are two preservative efficacy standards in the European Pharmacopoeia "A" and "B".

The standards identified above for the USP 27 are substantially identical to the requirements set forth in prior editions of the USP, particularly USP 24, USP 25 and USP 26.

The compositions of the present invention may also include one or more low molecular weight amino alcohols. The amino alcohols which may be utilized in the present invention are water-soluble and have a molecular weight in the range of from about 60 to about 200. The following compounds are representative of the low molecular weight amino alcohols which may be utilized in the present invention: 2-amino-2-methyl-1-propanol (AMP), 2-dimethylamino-methyl-1-propanol (DMAMP), 2-amino-2-ethyl-1,3-propanediol (AEPD), 2-amino-2-methyl-1,3-propanediol (AMPD), 2-amino-1-butanol (AB). "AMP (95%)", which refers to 95% pure AMP and 5% water, is the most preferred low molecular weight amino alcohol of the present invention. These amino alcohols are available commercially from Angus Chemical Company (Buffalo Grove, Ill.).

The amount of amino alcohol used will depend on the molecular weight of the amino alcohol selected, and the presdermatological compositions, but is particularly useful in ophthalmic compositions. Examples of such compositions include: ophthalmic pharmaceutical compositions, such as topical compositions used in the treatment of glaucoma, infections, allergies or inflammation; compositions for treating contact lenses, such as cleaning products and products for enhancing the ocular comfort of patients wearing contact lenses; and various other types of ophthalmic compositions, such as ocular lubricating products, artificial tears, astringents, and so on. The compositions may be aqueous or non-aqueous, but will generally be aqueous.

The ophthalmic pharmaceutical compositions of the present invention may contain various types of therapeutic agents. Examples of possible therapeutic agents include beta-blockers (e.g., timolol, betaxolol, levobetaxolol, carteolol, levobunolol, and propranolol), carbonic anhydrase inhibitors (e.g., brinzolamide and dorzolamide), alpha-1 antagonists (e.g., nipradolol), alpha-2 agonists (e.g. iopidine and brimonidine), miotics (e.g., pilocarpine and epinephrine), prostaglandin analogs (e.g., latanoprost, travoprost and unoprostone), hypotensive lipids (e.g., bimatoprost and compounds set forth in U.S. Pat. No. 5,352,708), neuroprotectants (e.g., memantine), serotonergics [e.g., 5-HT$_2$ agonists, such as S-(+)-1-(2-aminopropyl)-indazole-6-ol)], anti-angiogenesis agents (e.g., anecortave acetate), anti-infective agents (e.g., quinolones, such as moxifloxacin and gatifloxacin, and aminoglycosides, such as tobramycin and gentamicin), non-steroidal and steroidal anti-inflammatory agents (e.g., prednisolone, dexamethasone, lotoprednol, suprofen, diclofenac and ketorolac), growth factors (e.g., EGF), immunosuppressant agents (e.g., cyclosporin), and anti-allergic agents (e.g., olopatadine). The ophthalmic drug may be present in the form of a pharmaceutically acceptable salt, such as timolol maleate, brimonidine tartrate or sodium diclofenac. The compositions of the present invention may also include combinations of ophthalmic drugs, such as combinations of (i) a beta-blocker selected from the group consisting of betaxolol and timolol, and (ii) a prostaglandin analog selected from the group consisting of latanoprost, 1,5-keto latanoprost, travoprost, bimatoprost, and unoprostone isopropyl. In the event the therapeutic agent selected is anionic in an aqueous solution at an ophthalmically acceptable pH level, the amounts of zinc and borate or borate/polyol buffers required to self-preserve such compositions may need to be increased somewhat, due to interactions between the therapeutic agent and zinc ions.

The present invention is particularly directed to the provision of self-preserved, multi-dose ophthalmic compositions in connection with the treatment of conditions wherein the cornea or adjacent ocular tissues are irritated, or conditions requiring frequent application of a composition, such as in the treatment of dry eye patients. The self-preserved compositions of the present invention are therefore particularly useful in the field of artificial tears, ocular lubricants, and other compositions used to treat dry eye conditions, as well as other conditions involving ocular inflammation or discomfort.

The ophthalmic compositions of the present invention may be formulated to include one or more agents to enhance ocular comfort and/or retention of the compositions on the eye following topical application. The types of agents which may be utilized include: cellulose derivatives, such as hydroxypropyl methylcellulose ("HPMC"); Dextran 70; polyethylene glycol; propylene glycol; carboxy vinyl polymers; polyvinyl alcohol polymers or copolymers; and polysaccharides. The preferred polysaccharides are hydroxypropyl guar and other galactomannan polymers described in U.S. Pat. No. 6,583, 124 (Asgharian). The entire contents of the '124patent are hereby incorporated in the present specification by reference.

Some of the agents described in the preceding paragraph (e.g., hydroxypropyl guar, referred to hereinafter as "hp-guar") are capable of forming complexes with borate. The formation of such complexes may hamper the antimicrobial activity of the borate/amino alcohol system described herein. In the event such interference is encountered, adjustments to the system may be required. For example, the borate concentration can be increased, but this may result in an undesirable increase in the viscosity of the composition. The present invention is based in-part on a finding that the adverse impact of such polymers on the antimicrobial activity of the borate/amino alcohol system can be overcome by including zinc in the compositions.

The compositions of the present invention will generally be formulated as sterile aqueous solutions. The compositions of the present invention will be formulated so as to be compatible with the eye and/or other tissues to be treated with the compositions. The ophthalmic compositions intended for direct application to the eye will be formulated so as to have a pH and tonicity which are compatible with the eye. A buffer may be required so as to maintain the pH of the compositions with a range of 6.0 to 8.5, and may require a tonicity agent to bring the osmolality of the composition to a level at or near 210-350 milliosmoles per kilogram (mOsm/kg).

One or more conventional antimicrobial preservatives (e.g., benzalkonium chloride and polyquaternium-1) can be present in the compositions of the present invention, if desired, but the compositions preferably do not contain any conventional antimicrobial preservatives. If utilized, such preservatives can be present in conventional amounts, but in view of the self-preserving properties of the compositions of the present invention, such conventional antimicrobial preservatives can also be utilized in much lower concentrations than would be required to satisfy preservative efficacy requirements if only the conventional antimicrobial preservative were present in amounts less than conventional amounts. Since the present compositions can be a self-preserved composition, if an anti-microbial preservative is present as an option, the amount can be an amount that would not be effective alone as an antimicrobial preservative agent. However, the overall composition would have sufficient antimicrobial activity to satisfy USP/FDA/ISO preservative efficacy requirements.

Preferably the conventional antimicrobial preservative, if present, is not anionic and if anionic, it is preferred that the amount should be low enough to not substantially interfere with the antimicrobial activity of the preservative systems described herein.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

The following examples are presented to further illustrate selected embodiments of the present invention.

Example 1

The formulation shown in Table 1 below was prepared to evaluate the effect of a pH of 7.9 on the antimicrobial activity of the formulation.

TABLE 1

| Component | FID 103777<br>Lot Number 17110-01<br>Concentration (w/v %) |
|---|---|
| Dextran 70 | 0.1 |
| HPMC | 0.3 |
| Propylene Glycol | 0.3 |

TABLE 1-continued

| Component | FID 103777<br>Lot Number 17110-01<br>Concentration (w/v %) |
|---|---|
| Boric acid | 0.8 |
| Sorbitol | 1.4 |
| Sodium chloride | 0.1 |
| Potassium chloride | 0.12 |
| Calcium chloride | 0.0053 |
| Magnesium chloride | 0.0064 |
| Zinc chloride | 0.00015 |
| AMP (95%) | 0.588 |
| pH | 7.9 |

The formulation described in Table 1 was prepared as follows:

HPMC Solution:
1. In a 250 mL Pyrex media bottle, add the correct amount of 2% HPMC stock solution.
2. Autoclave at 121° C. for 30 minutes.
3. Hold the autoclaved solution for later compounding.

Buffer Vehicle:
1. In a 250 mL beaker, add the remaining formulation chemicals for a 200 mL batch using only 150 mL of purified water.
2. Measure the pH and adjust to 7.9 with NaOH/HCl.
3. QS to 100% (150 mL) with purified water.
4. Filter the solution using a 0.2 μm CA filter unit.

Final Formulation:
1. Slowly add the filtered buffer vehicle to the autoclaved HPMC stock solution.
2. Allow the solution to mix well.

The antimicrobial activity of the above-described solution was evaluated by means of a standard microbiological analysis (i.e., USP26 Antimicrobial Effectiveness Test). The test samples were challenged with standardized suspensions of five microorganisms, and the number of surviving microorganisms was determined at 7, 14 and 28 days. The results are presented in Table 2 below:

TABLE 2

| Microorganism | Time (days) | Log$_{10}$ Reduction of Survivors Lot Number 17110-01 |
|---|---|---|
| A. niger | 7 | 2.0 |
| | 14 | 2.1 |
| | 28 | 2.9 |
| C. albicans | 7 | 0.4 |
| | 14 | 1.4 |
| | 28 | 3.0 |
| E. coli | 7 | 2.2 |
| | 14 | 5.1 |
| | 28 | 5.1 |
| P. aeruginosa | 7 | 2.5 |
| | 14 | 5.0 |
| | 28 | 5.0 |
| S. aureus | 7 | 2.1 |
| | 14 | 4.6 |
| | 28 | 4.8 |

The results demonstrate overall preservative efficacy against the organisms tested.

Example 2

As explained above, polymers that are capable of forming complexes with borates (e.g., guar or hp-guar) have been found to reduce the antimicrobial activity of the borate/amino alcohol systems described herein. The formulation shown in Table 3 below is similar to the formulation described in Example 1, except that Dextran 70 and HPMC have been replaced by hp-guar.

A formulation nearly identical to the one shown in Table 3 was evaluated to determine if it had adequate antimicrobial activity to satisfy USP preservative efficacy requirements. It was determined that inclusion of hp-guar prevented the formulation from consistently satisfying the USP preservative efficacy requirements. However, it was discovered that this problem could be overcome by increasing the concentration of zinc chloride by a factor of 10 (i.e., from 0.00015 to 0.0015 w/v %). The formulation shown in Table 3, which contains this higher concentration of zinc chloride, has consistently satisfied the USP preservative efficacy requirements. The preservative efficacy test ("PET") results for four different lots are provided below:

TABLE 3

Formulation Number FID 105783/Concentration (w/v %)

| Component | FID 105783 |
|---|---|
| HP-Guar | 0.16 |
| Boric Acid | 0.7 |
| Sorbitol | 1.4 |
| PEG-400 | 0.4 |
| Propylene Glycol | 0.3 |
| Potassium Chloride | 0.12 |
| Sodium Chloride | 0.1 |
| Calcium Chloride | 0.0053 |
| Magnesium Chloride | 0.0064 |
| Zinc Chloride | 0.0015 |
| AMP (95%) | 0.57 |
| Hydrochloric Acid | Adj. pH |
| Target pH | 7.9 |
| Purified Water | QS to 100% |
| Volume to make (L) | 1 |

| | Lot Number | | | |
|---|---|---|---|---|
| PET Results | PD Lot | 03-34508 | 03-34433 | 03-34632 |
| P. aeruginosa (Day 7) | 5.0 | 5.0 | 4.8 | 5.0 |
| E. coli (Day 7) | 5.0 | 5.0 | 4.9 | 5.0 |
| P. aeruginosa (Day 14) | 5.0 | 5.0 | 4.8 | 5.0 |
| E. coli (Day 14) | 5.0 | 5.0 | 4.9 | 5.0 |
| P. aeruginosa (Day 28) | 3.9* | 3.9* | 4.8 | ND |
| E. coli (Day 28) | 4.0* | 4.0* | 4.9 | ND |

*Rechallenge on day 14
**ND = Not Performed

Example 3

The formulations shown in Tables 4 and 5 below were prepared and tested in order to evaluate the effect of small variations in pH on the antimicrobial activity of the compositions.

TABLE 4

Effect of pH

Formulation Number/Concentrations (w/v %)

| | FID 105784 | FID 105801 | FID 105802 | FID 105782 |
|---|---|---|---|---|
| | | Batch/Lot | | |
| | 03-34662 | 03-34667 | 03-34669 | 03-34648 |
| Component | | | | |
| HP-Guar | 0.16 | 0.16 | 0.16 | 0.16 |
| Boric Acid | 0.7 | 0.7 | 0.7 | 0.7 |

TABLE 4-continued

Effect of pH

| | Formulation Number/Concentrations (w/v %) | | | |
|---|---|---|---|---|
| | FID 105784 | FID 105801 | FID 105802 | FID 105782 |
| | Batch/Lot | | | |
| | 03-34662 | 03-34667 | 03-34669 | 03-34648 |
| Sorbitol | 1.4 | 1.4 | 1.4 | 1.4 |
| PEG-400 | 0.4 | 0.4 | 0.4 | 0.4 |
| Propylene Glycol | 0.3 | 0.3 | 0.3 | 0.3 |
| Potassium Chloride | 0.12 | 0.12 | 0.12 | 0.12 |
| Sodium Chloride | 0.1 | 0.1 | 0.1 | 0.1 |
| Calcium Chloride | 0.0053 | 0.0053 | 0.0053 | 0.0053 |
| Magnisium Chloride | 0.0064 | 0.0064 | 0.0064 | 0.0064 |
| Zinc Chloride | 0.00075 | 0.00075 | 0.00075 | 0.00075 |
| AMP (95%) | 0.6 | 0.6 | 0.6 | 0.6 |
| Hydrochloric Acid | Adj. pH | Adj. pH | Adj. pH | Adj. pH |
| Target pH | 7.0 | 7.3 | 7.6 | 7.9 |
| Purified Water | QS to 100% | QS to 100% | QS to 100% | QS to 100% |
| Volume to make (L) | 1 | 1 | 1 | 1 |
| PET Results (Day 7) | | | | |
| P. aeruginosa | −0.5 | −0.6 | −0.2 | 2.1 |
| E. coli | −0.5 | 0.1 | 3.3 | 5.0 |

The results presented in Table 4 show that as the pH of the formula is increased, the activity against the test organisms consistently improved. At a pH of 7.9, the composition satisfied the USP 26 preservative efficacy requirements. However, the compositions having a pH of less than 7.9 did not have adequate antimicrobial activity to satisfy the USP requirements.

The antimicrobial activities of two formulations that were identical except for pH were also compared. As shown in Table 5 below, the formulation having a pH of 7.7 did not satisfy USP 26 preservative efficacy requirements, but the formulation having a pH of 7.9 did meet those requirements.

TABLE 5

Effect of pH

| Component | Concentration (w/v %) | Concentration (w/v %) |
|---|---|---|
| HP-Guar | 0.16 | 0.16 |
| Boric Acid | 0.7 | 0.7 |
| Sorbitol | 1.4 | 1.4 |
| PEG-400 | 0.4 | 0.4 |
| Propylene Glycol | 0.3 | 0.3 |
| Potassium Chloride | 0.12 | 0.12 |
| Sodium Chloride | 0.1 | 0.1 |
| Calcium Chloride | 0.0053 | 0.0053 |
| Magnesium Chloride | 0.0064 | 0.0064 |
| Zinc Chloride | 0.0015 | 0.0015 |
| AMP (95%) | 0.6 | 0.6 |
| HCl/Adjust pH to | 7.9 | 7.7 |
| Purified Water | QS 100 | QS 100 |
| Microbiology | Passes USP | Fails USP |

Example 4

The formulations shown in Table 6 below were prepared in order to evaluate the effect of zinc chloride on antimicrobial activity. The first two solutions, which contained no zinc and 1.5 ppm of zinc chloride, respectively, did not satisfy the USP 26 preservative efficacy requirements, but the third solution, which contained 15 ppm of zinc chloride, did meet those requirements.

TABLE 6

Effect of Zinc Level

| | Formulation Number/Concentrations (w/v %) | | |
|---|---|---|---|
| | FID 105689 | FID 104706 | FID 105688 |
| | Batch/Lot | | |
| | 03-34434 | 03-34405 | 03-34433 |
| Component | | | |
| HP-Guar | 0.16 | 0.16 | 0.16 |
| Boric Acid | 0.7 | 0.7 | 0.7 |
| PEG-400 | 0.4 | 0.4 | 0.4 |
| Propylene Glycol | 0.3 | 0.3 | 0.3 |
| Sorbitol | 1.4 | 1.4 | 1.4 |
| Sodium Chloride | 0.1 | 0.1 | 0.1 |
| Potassium Chloride | 0.12 | 0.12 | 0.12 |
| Calcium Chloride | 0 | 0.0053 | 0.0053 |
| Magnesium Chloride | 0 | 0.0064 | 0.0064 |
| Zinc Chloride | 0 | 0.00015 | 0.0015 |
| AMP (95%) | 0.6 | 0.6 | 0.6 |
| Hydrochloric Acid | Adj. pH | Adj. pH | Adj. pH |
| Target pH | 7.9 | 7.9 | 7.9 |
| Purified Water | QS to 100% | QS to 100% | QS to 100% |
| PET Results (Day 7) | | | |
| P. aeruginosa | 2.6 | 0.7 | 4.8 |
| E. coli | 0.9 | 1.8 | 4.9 |

Example 5

The effect of zinc chloride on antimicrobial activity was further investigated by evaluating the preservative efficacy of the solutions shown in Table 7 below. The zinc chloride concentrations evaluated were 1.5 ppm, 3.0 ppm, 3.5 ppm, 7.5 ppm and 15 ppm, respectively. The results presented at the bottom of Table 7 show greater antimicrobial activity with increasing concentrations of zinc chloride. At 15 ppm, the two test organisms were totally eliminated (i.e., no survivors).

TABLE 7

Effect of Zinc Levels

| | Formulation Number/Concentration (w/v %) | | | | |
|---|---|---|---|---|---|
| | FID 104706 | FID 105780 | FID 105792 | FID 105782 | FID 105783 |
| | | | Batch/Lot | | |
| | 03-34628 | 03-34629 | 03-34652 | 03-34648 | 03-34632 |
| Component | | | | | |
| HP-Guar | 0.16 | 0.16 | 0.16 | 0.16 | 0.16 |
| Boric Acid | 0.7 | 0.7 | 0.7 | 0.7 | 0.7 |
| Sorbitol | 1.4 | 1.4 | 1.4 | 1.4 | 1.4 |
| PEG-400 | 0.4 | 0.4 | 0.4 | 0.4 | 0.4 |
| Propylene Glycol | 0.3 | 0.3 | 0.3 | 0.3 | 0.3 |
| Potassium Chloride | 0.12 | 0.12 | 0.12 | 0.12 | 0.12 |
| Sodium Chloride | 0.1 | 0.1 | 0.1 | 0.1 | 0.1 |
| Calcium Chloride | 0.0053 | 0.0053 | 0.0053 | 0.0053 | 0.0053 |
| Magnisium Chloride | 0.0064 | 0.0064 | 0.0064 | 0.0064 | 0.0064 |
| Zinc Chloride | 0.00015 | 0.0003 | 0.00045 | 0.00075 | 0.0015 |
| AMP (95%) | 0.6 | 0.6 | 0.6 | 0.6 | 0.6 |
| Hydrochloric Acid | Adj. pH | Adj. pH | Adj. pH | Adj. pH | Adj. pH |
| Target pH | 7.9 | 7.9 | 7.9 | 7.9 | 7.9 |
| Purified Water | QS to 100% | QS to 100% | QS to 100% | QS to 100% | QS to 100% |
| PET Results (Day 7) | | | | | |
| P. aeruginosa | 1.4 | 1.5 | 1.3 | 2.1 | 5.0 |
| E. coli | 1.0 | 2.1 | 3.9 | 5.0 | 5.0 |

Example 6

The role of amino alcohol concentration relative to antimicrobial activity was also investigated. The formulations shown in Table 8 below, which were identical except for the concentration of the amino alcohol AMP (95%), were utilized in this evaluation. As shown at the bottom of Table 8, the solutions containing AMP (95%) at concentrations of 0.2 and 0.4 w/v % did not satisfy the USP 26 preservative efficacy requirements against *Pseudomonas aeruginosa*, but the solution containing AMP (95%) at a concentration of 0.6 w/v % did meet those requirements.

TABLE 8

Amino Alcohol Concentration

| | Formulation Number/Concentration (w/v %) | | |
|---|---|---|---|
| | FID 105799 | FID 105800 | FID 105782 |
| | | Batch/Lot | |
| | 03-34665 Conc. (%) | 03-34666 Conc. (%) | 03-34648 Conc. (%) |
| Component | | | |
| HP-Guar | 0.16 | 0.16 | 0.16 |
| Boric Acid | 0.7 | 0.7 | 0.7 |
| Sorbitol | 1.4 | 1.4 | 1.4 |
| PEG-400 | 0.4 | 0.4 | 0.4 |
| Propylene Glycol | 0.3 | 0.3 | 0.3 |
| Potassium Chloride | 0.12 | 0.12 | 0.12 |
| Sodium Chloride | 0.1 | 0.1 | 0.1 |
| Calcium Chloride | 0.0053 | 0.0053 | 0.0053 |
| Magnisium Chloride | 0.0064 | 0.0064 | 0.0064 |
| Zinc Chloride | 0.00075 | 0.00075 | 0.00075 |
| AMP (95%) | 0.2 | 0.4 | 0.6 |
| Hydrochloric Acid | Adj. pH | Adj. pH | Adj. pH |
| Target pH | 7.9 | 7.9 | 7.9 |
| Purified Water | QS to 100% | QS to 100% | QS to 100% |
| Volume to make (L) | 1 | 1 | 1 |
| PET Results (Day 7) | | | |
| P. aeruginosa | −0.7 | −0.2 | 2.1 |
| E. coli | 5.0 | 4.9 | 5.0 |

Example 7

The above-described preservative system was also evaluated relative to ophthalmic formulations containing the therapeutic agents travoprost and patanol, respectively. The results of show that these compositions are projected to satisfy preservative efficacy requirements.

TABLE 9

| COMPONENT | % w/v | % w/v | % w/v | % w/v | % w/v | % w/v | % w/v |
|---|---|---|---|---|---|---|---|
| AL6221 | 0.004 | 0.004 | 0.004 | 0.004 | 0.004 | 0.004 | 0.004 |
| Polyoxyl 40 HCO | 0.5 | 0.5 | 0.5 | 0.5 | 0.5 | 0.5 | 0.75 |
| Zinc Chloride | 0.0025 | 0.0025 | 0.0025 | 0.0025 | 0.0025 | 0.0025 | 0.0025 |
| Boric Acid | 1 | 1 | 1 | 1 | 1 | 1 | 1 |

TABLE 9-continued

| COMPONENT | % w/v | % w/v | % w/v | % w/v | % w/v | % w/v | % w/v |
|---|---|---|---|---|---|---|---|
| Sorbitol | 0.25 | 0.25 | 0.25 | 0.25 | 0.25 | 0.25 | 0.25 |
| Propylene Glycol | 0 | 0.25 | 0.5 | 0.75 | 0.75 | 0.75 | 0.25 |
| NaOH/HCl q.s. pH | 6.0 | 6.0 | 6.0 | 6.0 | 6.0 | 6.0 | 6.0 |
| Purified Water q.s. 100% | 100 | 100 | 100 | 100 | 100 | 100 | 100 |
| Osmolality | 176 | 214 | 248 | 272 | 282 | 282 | 214 |
| 6 Hr. and 24 Hr. *Staph A.* | — | — | — | — | — | 0.0 & 0.1 | — |
| 6 and 24 Hr. *Pseudomonas* | — | — | — | — | — | 1.2 & 2.3 | — |
| 6 Hr. and 24 Hr. *E. Coli* | — | — | — | — | — | 1.0 & 1.5 | — |
| 7 Day *Staph A.* | 2.6 | 4.9 | 4.9 | 5.0 | 4.4 | 4.9 | 4.9 |
| 7 Day *Pseudomonas A.* | 4.6 | 5.0 | 5.0 | 4.0 | 5.1 | 5.1 | 5.0 |
| 7 Day *E. Coli* | 2.7 | 2.7 | 2.3 | 3.2$^d$ | 2.6 | 2.7 | 3.0 |
| 7 Day *Candida A.* | 0.1 | 0.0 | 0.2 | 0.2 | 0.2 | 0.2 | 0.0 |
| 7 Day *A. Niger* | 2.2 | 2.6 | 2.6 | 1.8 | 2.8 | 2.3 | 2.9 |

Example 8

The results obtained with the formulations shown below demonstrate the role of zinc concentration.

TABLE 10

| | FID Number | | | |
|---|---|---|---|---|
| | FID 105937 | FID 105935 | FID 105926 | FID 105936 |
| | Bacth/Lot | | | |
| | 03-34915 | 03-34913 | 03-34904 | 03-34914 |
| AL-12355 (HP-8A Guar) | 0.16 | 0.16 | 0.16 | 0.16 |
| Boric Acid | 1.0 | 1.0 | 1.0 | 1.0 |
| PEG-400 | 0.4 | 0.4 | 0.4 | 0.4 |
| Propylene Glycol | 0.3 | 0.3 | 0.3 | 0.3 |
| Potassium Chloride | 0.13 | 0.13 | 0.13 | 0.13 |
| Calcium Chloride | 0.0053 | 0.0053 | 0.0053 | 0.0053 |
| Magnesium Chloride | 0.0064 | 0.0064 | 0.0064 | 0.0064 |
| Zinc Chloride | N/A | 0.00075 | 0.0015 | 0.00225 |
| Sodium Hydroxide | Adj. pH | Adj. pH | Adj. pH | Adj. pH |
| Tris | N/A | N/A | N/A | N/A |
| Hydrochloric Acid | Adj. pH | Adj. pH | Adj. pH | Adj. pH |
| Target pH | 7.4 | 7.4 | 7.4 | 7.4 |
| Purified Water | QS to 100% | QS to 100% | QS to 100% | QS to 100% |
| 7 days *P. aeruginosa* | 0.6 | 2.1 | 3.9 | 3.2 |
| 7 days *E. coli* | 0.1 | 3.1 | 5.0 | 5.0 |
| 14 days *P. aeruginosa* | N/A | 2.9 | 5.1 | 4.3 |
| 14 days *E. coli* | N/A | 3.4 | 5.0 | 5.0 |
| 28 days *P. aeruginosa* | N/A | N/A | 5.1 | 5.1 |
| 28 days *E. coli* | N/A | N/A | 5.0 | 5.0 |

Example 9

The following formulations further illustrate the efficacy of preservative systems containing zinc and borate/polyol complexes.

TABLE 11

| | FID Number | | | | | |
|---|---|---|---|---|---|---|
| | FID 105973 | FID 105974 | FID 105975 | FID 105976 | FID 105977 | FID 105978 |
| | Bacth/Lot | | | | | |
| | 03-34977 | 03-34978 | 03-34979 | 03-34980 | 03-34981 | 03-34982 |
| Boric Acid | 1.0 | 1.0 | 1.0 | 1.0 | 1.0 | 1.0 |
| Propylene Glycol | 0.4 | 0.4 | 0.4 | 0.4 | 0.4 | 0.4 |
| Zinc Chloride | 0.0015 | 0.0015 | 0.0015 | 0.0015 | 0.0015 | 0.0015 |
| Polyoxyl 40 Hydrogenated Castor Oil | 0.5 | 0.05 | 0.5 | 0.5 | 0.5 | 0.5 |
| Disodium EDTA | N/A | 0.05 | 0.05 | N/A | 0.05 | 0.05 |
| Polyquad | N/A | N/A | 0.001 | N/A | N/A | 0.001 |
| Tromethamine | Adj. pH | Adj. pH | Adj. pH | Adj. pH | Adj. pH | Adj. pH |
| Hydrochloric Acid | Adj. pH | Adj. pH | Adj. pH | Adj. pH | Adj. pH | Adj. pH |
| Target pH | 6.0 | 6.0 | 6.0 | 6.0 | 6.0 | 6.0 |
| Purified Water | QS to 100% | QS to 100% | QS to 100% | QS to 100% | QS to 100% | QS to 100% |
| 7 days *P. aeruginosa* | 5.1 | 5.1 | 5.1 | 5.1 | 5.1 | 5.1 |
| 7 days *E. coli* | 3.3 | 1.6 | 4.9 | 3.9 | 0.6 | 4.9 |
| 14 days *P. aeruginosa* | 5.1 | 5.1 | 5.1 | 5.1 | NT | 5.1 |
| 14 days *E. coli* | 4.9 | 1.9 | 4.9 | 4.9 | NT | 4.9 |

TABLE 11-continued

| | ID Number | | | | |
|---|---|---|---|---|---|
| | FID 105982 | FID 105983 | FID 105984 Bacth/Lot | FID 105985 | FID 105986 |
| | 03-034988 | 03-034989 | 03-34990 | 03-34991 | 03-34992 |
| Boric Acid | 1.0 | 1.0 | 1.0 | 1.0 | 1.0 |
| Propylene Glycol | 0.4 | 0.4 | 0.4 | 0.4 | 0.4 |
| Zinc Chloride | 0.0015 | 0.0015 | 0.0015 | 0.0015 | 0.0015 |
| Polyoxyl 40 Stearate | 0.1 | 0.1 | 0.1 | 0.1 | 0.1 |
| Sodium Hydroxide | N/A | N/A | N/A | Adj. pH | Adj. pH |
| Hydrochloric Acid | Adj. pH | Adj. pH | Adj. pH | Adj. pH | Adj. pH |
| Target pH | 7.4 | 7.55 | 7.7 | 7.4 | 7.55 |
| Purified Water | QS to 100% | QS to 100% | QS to 100% | QS to 100% | QS to 100% |
| 7 days *P. aeruginosa* | 4.9 | 4.9 | 4.9 | 4.9 | 4.9 |
| 7 days *E. coli* | 4.3 | 3.8 | 3.9 | 4.9 | 4.9 |
| 14 days *P. aeruginosa* | 4.9 | 4.9 | 4.9 | 4.9 | 4.9 |
| 14 days *E. coli* | 4.9 | 4.9 | 4.9 | 4.9 | 4.9 |

NT = Not tested due to Day 7 Failure

We claim:

1. A multi-dose, self-preserved ophthalmic composition, said composition comprising:
   a therapeutically effective amount of an ophthalmic therapeutic agent selected from the group consisting of beta-blockers, carbonic anhydrase inhibitors, prostaglandin analogs, neuroprotectants, anti-angiogenesis agents, quinolones, anti-inflammatory agents, growth factors, immunosuppressant agents and anti-allergic agents; and
   a preservative system consisting essentially of:
   i. borate at a concentration in the composition of 0.3 to 1.5 w/v % wherein the borate comprises one or more borates;
   ii. polyol at a concentration in the composition of 0.6 to 2.0 w/v % wherein the polyol comprises sorbitol and propylene glycol; and
   iii. zinc ions, wherein the zinc ions are provided by zinc chloride at a concentration in the composition of 0.0005 to 0.005 w/v %;
   wherein the preservative system has sufficient antimicrobial activity to allow the composition to satisfy USP 26 preservative efficacy requirements.

2. A composition as in claim 1 wherein the therapeutic agent is a prostaglandin analog.

3. A composition as in claim 1 wherein the therapeutic agent is travoprost.

4. A method of enhancing the antimicrobial activity of an aqueous ophthalmic pharmaceutical composition, which comprises including a preservative system in the composition, the preservative system consisting essentially of:
   i. borate at a concentration in the composition of 0.3 to 1.5 w/v % wherein the borate comprises one or more borates;
   ii. polyol at a concentration in the composition of 0.6 to 2.0 w/v % wherein the polyol comprises sorbitol and propylene glycol; and
   iii. zinc ions, wherein the zinc ions are provided by zinc chloride at a concentration in the composition of 0.0005 to 0.005 w/v %; wherein:
   i. the preservative system has sufficient antimicrobial activity to allow the composition to satisfy USP 26 preservative efficacy requirements; and
   ii. the composition includes a therapeutically effective amount of an ophthalmic therapeutic agent selected from the group consisting of beta-blockers, carbonic anhydrase inhibitors, prostaglandin analogs, neuroprotectants, anti-angiogenesis agents, quinolones, anti-inflammatory agents, growth factors, immunosuppressant agents and anti-allergic agents.

5. A method as in claim 4 wherein the therapeutic agent is a prostaglandin analog.

6. A method as in claim 4 wherein the therapeutic agent is travoprost.

7. A composition as in claim 1 wherein the concentration of borate in the composition is 0.5-1.2 w/v %.

8. A composition as in claim 3 wherein the concentration of borate in the composition is 0.5-1.2 w/v %.

9. A method as in claim 4 wherein the concentration of borate in the composition is 0.5-1.2 w/v %.

10. A method as in claim 6 wherein the concentration of borate in the composition is 0.5-1.2 w/v %.

* * * * *